(12) United States Patent
Linhardt et al.

(10) Patent No.: US 8,100,528 B2
(45) Date of Patent: Jan. 24, 2012

(54) COATING SOLUTIONS COMPRISING SEGMENTED INTERACTIVE BLOCK COPOLYMERS

(75) Inventors: Jeffrey G. Linhardt, Fairport, NY (US); Devon A. Shipp, Potsdam, NY (US); Jay F. Kunzler, Canandaigua, NY (US); David Paul Vanderbilt, Webster, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 251 days.

(21) Appl. No.: 12/334,619

(22) Filed: Dec. 15, 2008

(65) Prior Publication Data
US 2009/0168012 A1 Jul. 2, 2009

Related U.S. Application Data

(60) Provisional application No. 61/016,844, filed on Dec. 27, 2007, provisional application No. 61/016,845, filed on Dec. 27, 2007, provisional application No. 61/016,841, filed on Dec. 27, 2007, provisional application No. 61/016,843, filed on Dec. 27, 2007.

(51) Int. Cl.
| G02C 7/04 | (2006.01) |
|---|---|
| C08F 130/08 | (2006.01) |
| A61F 2/24 | (2006.01) |
| A61F 2/16 | (2006.01) |
| A61F 2/06 | (2006.01) |
| A61F 2/14 | (2006.01) |
| A61F 2/12 | (2006.01) |
| A61F 2/02 | (2006.01) |

(52) U.S. Cl. ............ 351/160 H; 526/279; 623/2.1; 623/6.62; 623/1.46; 623/5.11; 623/11.11; 623/8

(58) Field of Classification Search .................. None
See application file for complete search history.

(56) References Cited

U.S. PATENT DOCUMENTS

| 4,136,250 A | 1/1979 | Mueller et al. |
|---|---|---|
| 4,153,641 A | 5/1979 | Deichert et al. |
| 4,168,112 A * | 9/1979 | Ellis et al. .................. 351/160 H |
| 4,327,203 A | 4/1982 | Deichert et al. |
| 4,355,147 A | 10/1982 | Deichert et al. |
| 4,740,533 A | 4/1988 | Su et al. |
| 4,910,277 A | 3/1990 | Bambury et al. |

(Continued)

FOREIGN PATENT DOCUMENTS

JP 2007/206166 8/2007

(Continued)

OTHER PUBLICATIONS

Machine translation of JP-2007-206166, translation made, Dec. 2010.*

(Continued)

*Primary Examiner* — Robert Loewe
(74) *Attorney, Agent, or Firm* — Glenn D. Smith

(57) ABSTRACT

This invention is directed toward surface treatment of a device. The surface treatment comprises the attachment of interactive segmented block copolymers to the surface of the substrate by means of interactive functionalities of the segmented block copolymer reacting with complementary surface functionalities in monomeric units along the polymer substrate. The present invention is also directed to a surface modified medical device, examples of which include contact lenses, intraocular lenses, vascular stents, phakic intraocular lenses, aphakic intraocular lenses, corneal implants, catheters, implants, and the like, comprising a surface made by such a method.

19 Claims, 1 Drawing Sheet

U.S. PATENT DOCUMENTS

| | | | |
|---|---|---|---|
| 4,954,587 A | 9/1990 | Mueller | |
| 5,010,141 A | 4/1991 | Mueller | |
| 5,034,461 A | 7/1991 | Lai et al. | |
| 5,070,215 A | 12/1991 | Bambury et al. | |
| 5,079,093 A * | 1/1992 | Akashi et al. | 428/411.1 |
| 5,079,319 A | 1/1992 | Mueller | |
| 5,260,000 A | 11/1993 | Nandu et al. | |
| 5,270,418 A | 12/1993 | Kunzler et al. | |
| 5,310,779 A | 5/1994 | Lai | |
| 5,321,108 A | 6/1994 | Kunzler et al. | |
| 5,358,995 A | 10/1994 | Lai et al. | |
| 5,387,662 A | 2/1995 | Kunzler et al. | |
| 5,449,729 A | 9/1995 | Lai | |
| 5,512,205 A | 4/1996 | Lai | |
| 5,610,252 A | 3/1997 | Bambury et al. | |
| 5,616,757 A | 4/1997 | Bambury et al. | |
| 5,708,094 A | 1/1998 | Lai et al. | |
| 5,710,302 A * | 1/1998 | Kunzler et al. | 556/434 |
| 5,714,557 A | 2/1998 | Kunzler et al. | |
| 5,804,318 A * | 9/1998 | Pinchuk et al. | 428/421 |
| 5,908,906 A | 6/1999 | Kunzler et al. | |
| 6,127,507 A * | 10/2000 | Santerre | 528/66 |
| 6,193,369 B1 | 2/2001 | Valint, Jr. et al. | |
| 6,200,626 B1 * | 3/2001 | Grobe et al. | 427/2.24 |
| 6,213,604 B1 | 4/2001 | Valint, Jr. et al. | |
| 6,274,133 B1 * | 8/2001 | Hu et al. | 424/78.04 |
| 6,323,165 B1 * | 11/2001 | Heiler et al. | 510/112 |
| 6,428,839 B1 | 8/2002 | Kunzler et al. | |
| 6,451,871 B1 * | 9/2002 | Winterton et al. | 523/106 |
| 6,486,213 B1 * | 11/2002 | Chen et al. | 514/772.1 |
| 6,550,915 B1 | 4/2003 | Grobe, III | |
| 6,599,559 B1 | 7/2003 | McGee et al. | |
| 6,793,973 B2 * | 9/2004 | Winterton et al. | 427/393.5 |
| 6,849,671 B2 * | 2/2005 | Steffen et al. | 523/107 |
| 6,858,310 B2 * | 2/2005 | McGee et al. | 428/447 |
| 6,891,010 B2 | 5/2005 | Kunzler et al. | |
| 6,902,812 B2 * | 6/2005 | Valint et al. | 428/420 |
| 6,926,965 B2 * | 8/2005 | Qiu et al. | 428/411.1 |
| 6,958,169 B2 | 10/2005 | Kunzler et al. | |
| 7,473,740 B2 * | 1/2009 | Zard et al. | 525/329.4 |
| 7,553,880 B2 * | 6/2009 | Nicolson et al. | 523/106 |
| 2002/0120084 A1 * | 8/2002 | Valint et al. | 526/260 |
| 2002/0155241 A1 * | 10/2002 | Tarasevich et al. | 428/36.91 |
| 2003/0162905 A1 | 8/2003 | Benz et al. | |
| 2004/0236020 A1 * | 11/2004 | Tsuji et al. | 525/99 |
| 2005/0056553 A1 * | 3/2005 | Matsuzawa et al. | 206/5.1 |
| 2005/0107531 A1 | 5/2005 | Claude | |
| 2005/0203256 A1 * | 9/2005 | Destarac et al. | 525/337 |
| 2005/0205451 A1 * | 9/2005 | Brown-Skrobot et al. | 206/438 |
| 2006/0063904 A1 * | 3/2006 | Ketelson | 526/303.1 |
| 2006/0078587 A1 * | 4/2006 | Leong | 424/423 |
| 2006/0114409 A1 * | 6/2006 | Kunzler et al. | 351/160 R |
| 2006/0154544 A1 * | 7/2006 | Talingting-Pabalan et al. | 442/181 |
| 2006/0251694 A1 * | 11/2006 | Nielsen et al. | 424/422 |
| 2006/0292209 A1 * | 12/2006 | Lewandowski et al. | 424/445 |
| 2007/0010595 A1 * | 1/2007 | McCabe et al. | 523/106 |
| 2007/0026043 A1 | 2/2007 | Guan et al. | |
| 2007/0122540 A1 | 5/2007 | Salamone et al. | |
| 2007/0132120 A1 * | 6/2007 | Rastogi et al. | 264/1.1 |
| 2007/0154521 A1 | 7/2007 | Zhao | |
| 2007/0155907 A1 | 7/2007 | Zhao | |
| 2007/0264303 A1 | 11/2007 | Atanasoska et al. | |
| 2008/0174035 A1 * | 7/2008 | Winterton | 264/1.36 |
| 2010/0137517 A1 * | 6/2010 | Kennedy et al. | 525/94 |

FOREIGN PATENT DOCUMENTS

| | | |
|---|---|---|
| WO | WO 96/31792 | 10/1996 |
| WO | 2005/068571 | 7/2005 |
| WO | 2007/024500 | 3/2007 |

OTHER PUBLICATIONS

Mayadunne et al. Macromolecules, 2000, 33, 243-245.*
Karlgard et al. International Journal of Pharmaceutics, 2003, 257, 141-151.*
Alemany et al. J. Biomed. Mater. Res. (Appl. Biomater.) 2002, 63, 319-325.*
Database WPI Week 200776, Thomson Scientific, London, GB; AN 2007-809281; XP002523683.
Database WPI Week 200557, Thomson Scientific, London, GB; AN 2005-563975; XP002523684.
International Search Report (PCT/ISA/210) and Written Opinion (PCT/ISA/237) mailed on Apr. 29, 2009.
Lai, Yu-Chin, "The Role of Bulky Polysiloxanylalkyl Methacrylates in Polyurethane-Polysiloxane Hydrogels", Journal of Applied Polymer Science, vol. 60, 1193-1199 (1966).
EPO Communication pursuant to Article 94(3) EPC dated Feb. 1, 2011.

* cited by examiner

COATING SOLUTIONS COMPRISING SEGMENTED INTERACTIVE BLOCK COPOLYMERS

CROSS REFERENCE TO RELATED APPLICATIONS

This application claims the benefit of Provisional Patent Application No. 61/016,844 filed Dec. 27, 2007; Provisional Patent Application No. 61/016,845 filed Dec. 27, 2007; Provisional Patent Application No. 61/016,841 filed Dec. 27, 2007; and Provisional Patent Application No. 61/016,843 filed Dec. 27, 2007.

FIELD OF INVENTION

This invention relates to coating solutions comprising a new class of tailored polymers useful as surface coatings for ophthalmic devices. These polymers can be specifically tailored using controlled radical polymerization processes and contain a number of functional domains. Controlled radical polymerization allows the facile synthesis of segmented block copolymers with tunable chemical composition that, as a result, show different chemical properties than those prepared via conventional free radical polymerization. Segmented block copolymers with substrate binding domain(s) containing functional groups such as boronic acids, hydrogen bonding groups and electrostatic groups and hydrophilic domain(s) show good surface properties when interactively bound to substrates containing complimentary functionality.

BACKGROUND OF THE INVENTION

Medical devices such as ophthalmic lenses are made from a wide variety of materials. In the contact lens field materials are broadly categorized into conventional hydrogels or silicone hydrogels. Recently, the use of silicone-containing materials (silicone hydrogels) has been preferred. These materials can vary greatly in water content. However, regardless of their water content, silicone materials tend to be relatively hydrophobic, non-wettable, and have a high affinity for lipids. Methods to modify the surface of silicone devices by increasing their hydrophilicity and improving their biocompatibility are of great importance.

A number of copolymers for surface coatings have been investigated. U.S. Pat. No. 6,958,169 discloses providing a medical device formed from a monomer mixture comprising a hydrophilic device-forming monomer including a copolymerizable group and an electron donating moiety, and a second device-forming monomer including a copolymerizable group and a interactive functional group; and, contacting a surface of the medical device with a wetting agent including a proton donating moiety reactive with the functional group provided by the second lens-forming monomer and that complexes with the electron donating moiety provided by the hydrophilic lens-forming monomer.

U.S. Pat. No. 6,858,310 discloses a method of modifying the surface of a medical device to increase its biocompatibility or hydrophilicity by coating the device with a removable hydrophilic polymer by means of reaction between reactive functionalities on the hydrophilic polymer with functionalities that are complementary on or near the surface of the medical device.

U.S. Pat. No. 6,599,559 discloses a method of modifying the surface of a medical device to increase its biocompatibility or hydrophilicity by coating the device with a removable hydrophilic polymer by means of reaction between reactive functionalities on the hydrophilic polymer which functionalities are complementary to reactive functionalities on or near the surface of the medical device.

U.S. Pat. No. 6,428,839 discloses a method for improving the wettability of a medical device, comprising the steps of: (a) providing a medical device formed from a monomer mixture comprising a hydrophilic monomer and a silicone-containing monomer, wherein said medical device has not been subjected to a surface oxidation treatment; (b) contacting a surface of the medical device with a solution comprising a proton-donating wetting agent, whereby the wetting agent forms a complex with the hydrophilic monomer on the surface of the medical device in the absence of a surface oxidation treatment step and without the addition of a coupling agent.

Many copolymers are currently made using conventional free radical polymerization techniques with the structure of the polymer being completely random or controlled by the reactivity ratios of the respective monomers. By using controlled free radical polymerization techniques one is able to assemble copolymers in a controlled fashion and, in turn, they show completely different solution and coating properties than copolymers prepared using conventional free radical polymerization techniques. Controlled free radical polymerization can be conducted by a variety of methods, such as ATRP (atom transfer radical polymerization) and RAFT (Reversible addition-fragmentation chain transfer polymerization).

SUMMARY

In accordance with the present disclosure, the invention relates generally to coating solutions comprising interactive segmented block copolymers for forming bound coatings in the manufacture of medical devices. As used herein the terms "bound", "binding", or terms of similar import, refer to various chemical interactions such as, electrostatic, ionic, complexation, hydrogen bond or other interaction between the interactive segmented block copolymer and the surface functionality of the device which results in the association of the coating composition with the device. Examples of suitable devices include contact lenses, intraocular lenses, intraocular lens inserters, vascular stents, phakic intraocular lenses, aphakic intraocular lenses, corneal implants, catheters, implants, and the like.

Interactive segmented block copolymers prepared through Atom Transfer Radical Polymerization ("ATRP") methods in accordance with the invention herein may have the following generic formula (I):

$$R_1\text{-}[(A)_m]_p\text{-}[(B)_n]_q\text{-}X \qquad (I)$$

wherein $R_1$ is the reactive residue of a moiety capable of acting as an initiator for Atom Transfer Radical Polymerization, A is a chemical binding unit block, B is a hydrophilic unit block, m is 1 to 10,000, n is 1 to 10,000, p and q are natural numbers, and X is a halogen capping group of the initiator for Atom Transfer Radical Polymerization with the proviso that when A is an ionic block, B will be a nonionic block. It should be noted, that there are many processes for the post polymerization removal or transformation of the halogen capping group of an initiator for Atom Transfer Radical Polymerization which are known to one of ordinary skill in the art. Therefore polymers prepared using ATRP according to the invention herein would include those where X is a halogen capping group of the initiator for Atom Transfer Radical Polymerization and those polymers that have undergone post polymerization removal or transformation of the halogen capping group of an initiator for Atom Transfer Radical Polymerization (i.e., derivatized reaction product). The polymers which contain halogen end-groups can be utilized in a host of traditional alkyl halide organic reactions. In one example, the addition of tributyltin hydride to the polymeric alkyl halide in the presence of a radical source (AIBN, or Cu(I) complex) leads to a saturated hydrogen-terminated polymer. In another example, by replacing tributyltin hydride with allyl tri-n-butylstannane, polymers with allyl end groups can be prepared. The terminal halogen can also be displaced by nucleophilic substitution, free-radical chemistry, or electrophilic addition catalyzed by Lewis acids to yield a wide variety of telechelic derivatives, such as alkenes, alkynes, alcohols, thiols, alkanes, azides, amines, phosphoniums, or epoxy groups, to mention a few.

Interactive segmented block copolymers prepared through Reversible addition-fragmentation chain transfer polymerization ("RAFT") methods in accordance with the invention herein may have the following generic formula (II):

wherein $R_1$ is a radical forming residue of a RAFT agent or free radical initiator, A is a chemical binding unit block, B is a hydrophilic unit block, m is 1 to 10,000, n is 1 to 10,000, p and q are natural numbers, and $R_2$ is a thio carbonyl thio fragment of the chain transfer agent with the proviso that when A is an ionic block, B will be a nonionic block. RAFT agents based upon thio carbonyl thio chemistry are well known to those of ordinary skill in the art and would include, for example, xanthates, trithiocarbonates and dithio esters. It should be noted, that there are many processes for the post polymerization removal or transformation of the thio carbonyl thio fragment of the chain transfer agent which are known to one of ordinary skill in the art. Therefore polymers prepared using RAFT agent according to the invention herein would include those where $R_2$ is a thio carbonyl thio fragment of the chain transfer agent and those polymers that have undergone post polymerization removal or transformation of the thio carbonyl thio fragment of the chain transfer agent (i.e., a derivatized reaction product). One example of such a transformation is the use of free radical reducing agents to replace the thio carbonyl thio group with hydrogen. Others include thermolysis of the end group or conversion of the thio carbonyl thio groups to thiol groups by aminolysis. A wide variety of telechelic derivatives can be prepared, such as alkenes, alkynes, alcohols, thiols, alkanes, azides, amines, phosphoniums, or epoxy groups, to mention a few.

Interactive segmented block copolymers prepared through reversible addition-fragmentation chain transfer polymerization ("RAFT") methods in accordance with the invention herein may have the following generic formula (III):

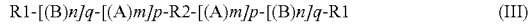

wherein R1 is a radical forming residue of a RAFT agent or free radical initiator, A is a chemical binding unit block, B is a hydrophilic unit block, m is 1 to 10,000, n is 1 to 10,000, p and q are natural numbers, and R2 is a thio carbonyl group.

For each of the polymers of generic formula I, II and III the order of the block units is not critical and the interactive segmented block copolymer can contain more than two blocks. Therefore the interactive segmented block copolymers can be multiblock copolymers and include repetition of one or more blocks. As examples please see the nonlimiting representations below, each of which is intended to fall within generic formula I, II and III:

Interactive segmented block copolymers according to the invention herein may also contain blocks that would not be considered to be binding or hydrophilic, for example, polystyrene or polymethyl methacrylate. The presence of non binding or non hydrophilic block(s) within a polymer is contemplated as being within the scope of the claimed interactive segmented block copolymers and formulae I, II and III of the invention herein.

Therefore, disclosed in certain embodiments herein is a method of forming a surface modified medical device, the method comprising providing a medical device having at least one group providing interactive functionality on at least one surface of the medical device; providing a surface modifying agent comprising a interactive segmented block copolymer comprising a hydrophilic block and a chemical binding unit block having reactivity that is complimentary to the at least one group providing surface functionality of the medical device; contacting the at least one surface having interactive functionality of the medical device with the surface modifying agent, and; subjecting the device surface and surface modifying agent to reaction conditions suitable for forming a chemical interaction selected from the group consisting of electrostatic, ionic, complexation or hydrogen bond interaction between the device surface and the surface modifying agent to form a surface modified medical device.

Also disclosed in certain embodiments herein is a surface modified medical device comprising a medical device having at least one group providing reactive functionality on at least one surface of the medical device; and a interactive segmented block copolymer comprising a chemical binding unit block and a hydrophilic block applied to the surface of the medical device; whereby a chemical interaction selected from the group consisting of electrostatic, ionic, complexation or hydrogen bond interaction occurs between the device surface and the surface modifying agent to form a surface modified medical device.

DETAILED DESCRIPTION

Figure 1:
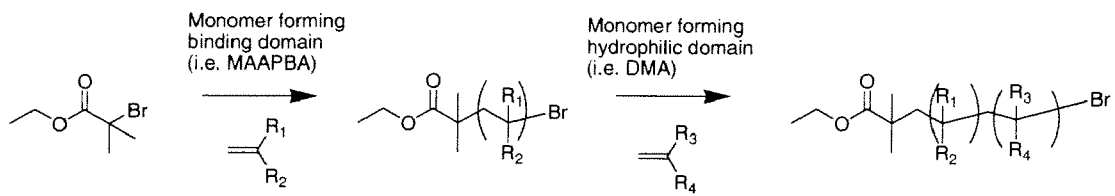
FIG. 1 is a schematic example of atom-transfer radical polymerization (ATRP) used to make a segmented block copolymer in which there is an oligomeric block of the chemical binding unit at one end of the polymer followed by a large hydrophilic block.

The present invention relates generally to coating solutions comprising interactive segmented block copolymers. Compositions comprising the interactive segmented block copolymers are useful in providing surface bound coatings in the manufacture of medical devices. In preferred embodiments, the present invention relates to interactive segmented block copolymers having interactive functionality that is complimentary to surface functionality of a medical device such as an ophthalmic lens. It should be understood that the term "surface" is not to be limited to meaning "at least one complete surface". Surface coverage does not have to be even or complete to be effective for surface functionality. The interactive segmented block copolymers of the present invention are useful as coatings for biocompatible materials including both soft and rigid materials commonly used for ophthalmic lenses, including contact lenses.

Interactive segmented block copolymers prepared through Atom Transfer Radical Polymerization ("ATRP") methods in accordance with the invention herein have the following generic formula (I):

$$R_1\text{-}[(A)_m]_p\text{-}[(B)_n]_q\text{-}X \quad (I)$$

wherein $R_1$ is the reactive residue of a moiety capable of acting as an initiator for Atom Transfer Radical Polymerization, A is a chemical binding unit block, B is a hydrophilic unit block, m is 1 to 10,000, n is 1 to 10,000, p and q are natural numbers, and X is a halogen capping group of the initiator for Atom Transfer Radical Polymerization with the proviso that when A is an ionic block, B will be a nonionic block. It would be recognized by one of ordinary skill in the art that X being an alkyl halide can be converted to another functionality through subsequent chemical reaction. It should be noted, that there are many processes for the post polymerization removal or transformation of the halogen capping group of an initiator for Atom Transfer Radical Polymerization which are known to one of ordinary skill in the art. Therefore polymers prepared using ATRP according to the invention herein would include those where X is a halogen capping group of the initiator for Atom Transfer Radical Polymerization and those polymers that have undergone post polymerization removal or transformation of the halogen capping group of an initiator for Atom Transfer Radical Polymerization (i.e., derivatized reaction product). The polymers which contain halogen end-groups can be utilized in a host of traditional alkyl halide organic reactions. In one example, the addition of tributyltin hydride to the polymeric alkyl halide in the presence of a radical source (AIBN, or Cu(I) complex) leads to a saturated hydrogen-terminated polymer. In another example, by replacing tributyltin hydride with allyl tri-n-butylstannane, polymers with allyl end groups can be prepared. The terminal halogen can also be displaced by nucleophilic substitution, free-radical chemistry, or electrophilic addition catalyzed by Lewis acids to yield a wide variety of telechelic derivatives, such as alkenes, alkynes, alcohols, thiols, alkanes, azides, amines, phosphoniums, or epoxy groups, to mention a few.

Interactive segmented block copolymers prepared through Reversible addition-fragmentation chain transfer polymerization ("RAFT") methods in accordance with the invention herein have the following generic formula (II):

$$R_1\text{-}[(A)_m]_p\text{-}[(B)_n]_q\text{-}R_2 \quad (II)$$

wherein $R_1$ is a radical forming residue of a RAFT agent or free radical initiator, A is a chemical binding unit block, B is a hydrophilic unit block, m is 1 to 10,000, n is 1 to 10,000, p and q are natural numbers, and $R_2$ is a thio carbonyl thio fragment of the chain transfer agent with the proviso that when A is an ionic block, B will be a nonionic block. It would be recognized by one of ordinary skill in the art that $R_2$ being a thio carbonyl thio fragment can be cleaved from the end of the polymer or converted to another functionality through subsequent chemical reaction. RAFT agents based upon thio carbonyl thio chemistry are well known to those of ordinary skill in the art and would include, for example, xanthates, trithiocarbonates and dithio esters. It should be noted, that there are many processes for the post polymerization removal or transformation of the thio carbonyl thio fragment of the chain transfer agent which are known to one of ordinary skill in the art. Therefore polymers prepared using RAFT agent according to the invention herein would include those where $R_2$ is a thio carbonyl thio fragment of the chain transfer agent and those polymers that have undergone post polymerization removal or transformation of the thio carbonyl thio fragment of the chain transfer agent (i.e., a derivatized reaction product). One example of such a transformation is the use of free radical reducing agents to replace the thio carbonyl thio group with hydrogen. Others include thermolysis of the end group or conversion of the thio carbonyl thio groups to thiol groups by aminolysis. A wide variety of telechelic derivatives can be prepared, such as alkenes, alkynes, alcohols, thiols, alkanes, azides, amines, phosphoniums, or epoxy groups, to mention a few.

Interactive segmented block copolymers prepared through reversible addition-fragmentation chain transfer polymerization ("RAFT") methods in accordance with the invention herein have the following generic formula (III):

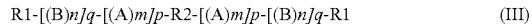

$$R1\text{-}[(B)n]q\text{-}[(A)m]p\text{-}R2\text{-}[(A)m]p\text{-}[(B)n]q\text{-}R1 \quad (III)$$

wherein R1 is a radical forming residue of a RAFT agent or free radical initiator, A is a chemical binding unit block, B is a hydrophilic unit block, m is 1 to 10,000, n is 1 to 10,000, p and q are natural numbers, and R2 is a thio carbonyl thio group.

For each of the polymers of generic formula I, II and III the order of the block units is not critical and the interactive segmented block copolymer can contain more than two blocks. Therefore the interactive segmented block copolymers can be multiblock copolymers and include repetition of one or more blocks. As examples please see the nonlimiting representations below, each of which is intended to fall within generic formula I, II and III:

$$\text{-}(A)_m\text{-}(B)_n\text{-} \quad (1)$$

$$\text{-}(B)_n\text{-}(A)_m\text{-} \quad (2)$$

$$\text{-}(A)_m\text{-}(B)_n\text{-}(A)_m\text{-} \quad (3)$$

Interactive segmented block copolymers according to the invention herein may also contain blocks that would not be considered to be binding or hydrophilic, for example, polystyrene or polymethyl methacrylate. The presence of non binding or non hydrophilic block(s) within a polymer is contemplated as being within the scope of the claimed reactive segmented block copolymers and formulae I, II and III of the invention herein.

The present invention provides materials useful for surface modifying contact lenses and like medical devices through the use of complementary interactive functionality. Although only contact lenses will be referred to hereinafter for purposes of simplicity, such reference is not intended to be limiting since the subject method is suitable for surface modification of other medical devices such as phakic and aphakic intraocular lenses and corneal implants as well as contact lenses. Surface interactive groups of the polymeric materials of the contact lenses and other biomedical devices are used to form chemical linkages, i.e., binding, with the interactive segmented block copolymers of the invention herein. The preferred interactive segmented block copolymers in the present invention are selected based on the specific interactive surface groups of the polymeric material to be coated. In accordance with the present invention, the one or more interactive segmented block copolymers selected for surface modification should have complementary interactive chemical functionality to that of the surface of the substrate. Such complementary interactive chemical functionality enables a chemical reaction between the interactive segmented block copolymers and the complementary surface functionality of the substrate to form electrostatic, ionic, complexation, hydrogen bond or other interactions there between. The one or more interactive segmented block copolymers are thus bound to the surface of the contact lens or like medical device to achieve surface modification thereof.

The interactive segmented block copolymer comprises a chemical binding unit block to provide the desired surface binding of the molecule. The chemical binding unit block can be varied and is determined based upon the intended use of the interactive segmented block copolymers. That is, the chemical binding unit block of the interactive segmented block copolymers is selected to provide functionality that is complementary with the surface functionality of the device. The chemical binding unit block will contain functional groups such as boronic acids, hydrogen bonding groups and electrostatic groups.

Selection of the chemical binding unit monomer of the block copolymer is determined by the functional groups on the surface of the device. For example, if the interactive molecule on the surface of the device contains a carboxylic acid group, a quaternary amine containing monomer can be a chemical binding unit monomer of the interactive segmented block copolymer. If the interactive molecule on the surface of the device contains hydroxy or amino functionality, boronic acid containing monomers can be a chemical binding unit monomer of the interactive segmented block copolymer. A wide variety of suitable combinations of functional group containing monomers of the chemical binding unit complementary to interactive groups on the surface of the device will be apparent to those of ordinary skill in the art. For example, the chemical binding unit block may comprise a moiety selected from styrene boronic acid, 3-methacrylamido styrene boronic acid, trimethyl, 2-methacryloyloxyethylsulfonate salts, 3-methacrylamidopropyl-N,N,N-trimethyammonium salts, 2-methacryloyloxyethyl-N,N,N-trimethylammonium salts, and amine-containing monomers, such as 3-methacrylamidopropyl-N,N-dimethyl amine. Examples of complementary functionality are provided below in Table 1.

TABLE 1

| MONOMER/RESIDUE HAVING A INTERACTIVE FUNCTIONAL GROUP | COMPLEMENTARY INTERACTIVE SURFACE FUNCTIONALITY |
|---|---|
| 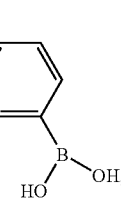 | Hydroxyl, amine, geminal diols, cis diols |
| 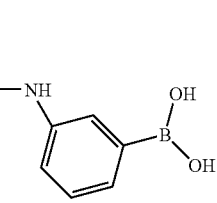 | |
| 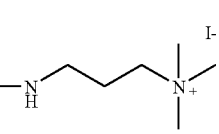 | Anionic groups, Carboxylic acid |
| 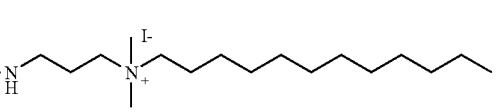 | |
| Carboxylic acids, sulfonic acids, phosphonic acids | Cationic groups |
| 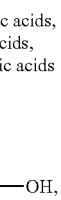 | |

TABLE 1-continued

| MONOMER/RESIDUE HAVING A INTERACTIVE FUNCTIONAL GROUP | COMPLEMENTARY INTERACTIVE SURFACE FUNCTIONALITY |
|---|---|
| 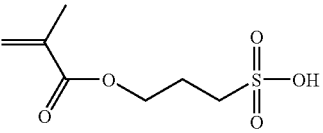 | |

The chemical binding unit block of the interactive segmented block copolymers is oligomeric or polymeric and is sized to provide suitable binding to the surface of the medical device to be coated. Therefore the variable m of formula I, II or III can be between 1 and about 1000, preferably between 1 and about 100, most preferably between 1 and about 30.

In addition to the chemical binding unit, the interactive segmented block copolymers of the invention herein will also contain hydrophilic domain(s) showing good surface properties when the block copolymer is covalently bound to substrates containing complimentary functionality. The hydrophilic domain(s) will comprise at least one hydrophilic monomer, such as, HEMA, glycerol methacrylate, methacrylic acid ("MAA"), acrylic acid ("AA"), methacrylamide, acrylamide, N,N'-dimethylmethacrylamide, or N,N'-dimethylacrylamide; copolymers thereof; hydrophilic prepolymers, such as ethylenically unsaturated poly(alkylene oxide)s, cyclic lactams such as N-vinyl-2-pyrrolidone ("NVP"), or derivatives thereof. Still further examples are the hydrophilic vinyl carbonate or vinyl carbamate monomers. Hydrophilic monomers can be nonionic monomers, such as 2-hydroxyethyl methacrylate ("HEMA"), 2-hydroxyethyl acrylate ("HEA"), 2-(2-ethoxyethoxy)ethyl(meth)acrylate, glyceryl (meth)acrylate, poly(ethylene glycol (meth)acrylate), tetrahydrofurfuryl(meth)acrylate, (meth)acrylamide, N,N'-dimethylmethacrylamide, N,N'-dimethylacrylamide ("DMA"), N-vinyl-2-pyrrolidone (or other N-vinyl lactams), N-vinyl acetamide, and combinations thereof. Still further examples of hydrophilic monomers are the vinyl carbonate and vinyl carbamate monomers disclosed in U.S. Pat. No. 5,070,215, and the hydrophilic oxazolone monomers disclosed in U.S. Pat. No. 4,910,277. The contents of these patents are incorporated herein by reference. The hydrophilic monomer also can be an anionic monomer, such as 2-methacryloyloxyethylsulfonate salts. Substituted anionic hydrophilic monomers, such as from acrylic and methacrylic acid, can also be utilized wherein the substituted group can be removed by a facile chemical process. Non-limiting examples of such substituted anionic hydrophilic monomers include trimethylsilyl esters of (meth)acrylic acid, which are hydrolyzed to regenerate an anionic carboxyl group. The hydrophilic monomer also can be a cationic monomer selected from the group consisting of 3-methacrylamidopropyl-N,N,N-trimethyammonium salts, 2-methacryloyloxyethyl-N,N,N-trimethylammonium salts, and amine-containing monomers, such as 3-methacrylamidopropyl-N,N-dimethyl amine. Other suitable hydrophilic monomers will be apparent to one skilled in the art.

The hydrophilic monomer block will be sized to provide the desirable surface coating property of the interactive segmented block copolymer. The size of the hydrophilic oligomeric or polymeric block may vary depending upon the substrate to be coated and the intended use. Therefore the variable n of formula I, II or III can be between 1 and about 10000, preferably between about 10 and about 1000, and more preferably between about 20 and about 300.

Figure 2:
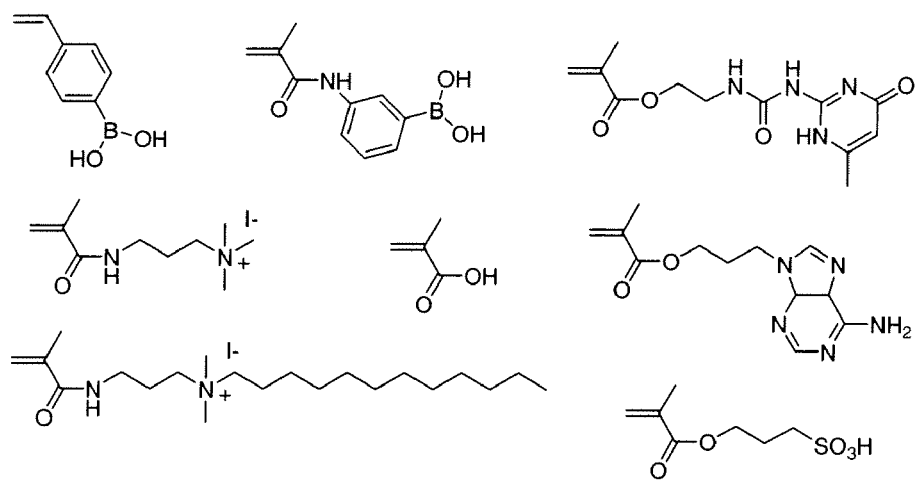
FIG. 2 is the structural formula of various monomers which may be used to provide the interactive functionality of the segmented block copolymers of the invention herein.
Figure 3:
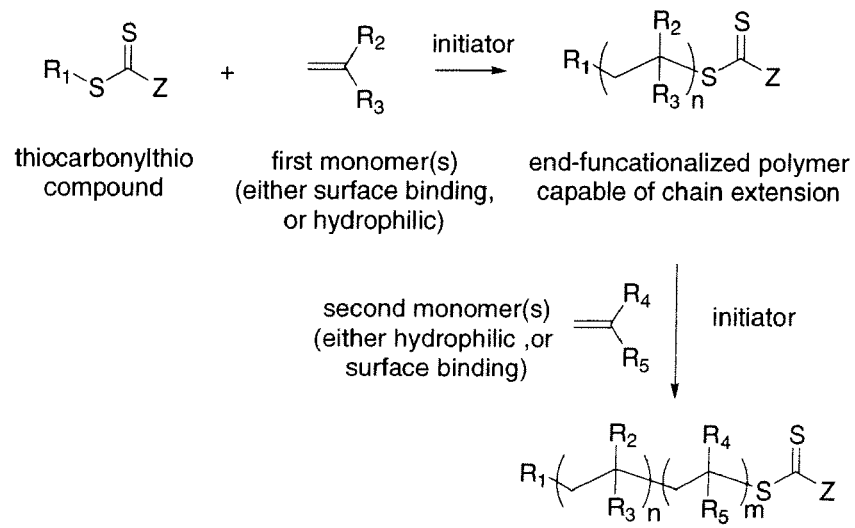
FIG. 3 is a reaction schematic showing how RAFT polymerization can be used to polymerize block copolymers with functional domains.

Atom-transfer radical polymerization (ATRP) can be used to prepare segmented block copolymers in which the molecular weight of each of the blocks and the entire polymer can be precisely controlled. As shown in FIG. 1, atom-transfer radical polymerization (ATRP) can be used to make a segmented block copolymer in which there is a block of the chemical binding unit at one end of the polymer followed by a large hydrophilic block. It should be understood that the order of addition of the monomer comprising the chemical binding unit domain and the monomer comprising the hydrophilic domain is not critical. A large number of monomers are available for the assembly of polymers (For example, see FIG. 2). Reversible addition-fragmentation chain transfer polymerization (RAFT) can also be used to prepare segmented block copolymers in which the molecular weight of each of the blocks and the entire polymer can be precisely controlled (see FIG. 3).

The interactive segmented block copolymers of the invention herein are useful in providing coatings for substrates. Examples of substrate materials useful with the present invention are taught in U.S. Pat. No. 5,908,906 to Künzler et al.; U.S. Pat. No. 5,714,557 to Künzler et al.; U.S. Pat. No. 5,710,302 to Künzler et al.; U.S. Pat. No. 5,708,094 to Lai et al.; U.S. Pat. No. 5,616,757 to Bambury et al.; U.S. Pat. No. 5,610,252 to Bambury et al.; U.S. Pat. No. 5,512,205 to Lai; U.S. Pat. No. 5,449,729 to Lai; U.S. Pat. No. 5,387,662 to Künzler et al.; U.S. Pat. No. 5,310,779 to Lai and U.S. Pat. No. 6,891,010 to Künzler et al.; which patents are incorporated by reference as if set forth at length herein.

The present invention contemplates the use of interactive segmented block copolymers with medical devices including both "hard" and "soft" contact lenses. As disclosed above, the invention is applicable to a wide variety of materials. Hydrogels in general are a well-known class of materials that comprise hydrated, cross-linked polymeric systems containing water in an equilibrium state. Silicon containing hydrogels generally have water content greater than about 5 weight percent and more commonly between about 10 to about 80 weight percent. Such materials are usually prepared by polymerizing a mixture containing at least one silicon containing monomer and at least one hydrophilic monomer. Typically, either the silicon containing monomer or the hydrophilic monomer functions as a crosslinking agent (a crosslinker being defined as a monomer having multiple polymerizable functionalities) or a separate crosslinker may be employed. Applicable silicon containing monomeric units for use in the formation of silicon containing hydrogels are well known in the art and numerous examples are provided in U.S. Pat. Nos. 4,136,250; 4,153,641; 4,740,533; 5,034,461; 5,070,215; 5,260,000; 5,310,779; and 5,358,995.

Examples of applicable silicon-containing monomeric units include bulky polysiloxanylalkyl(meth)acrylic monomers. An example of bulky polysiloxanylalkyl (meth)acrylic monomers are represented by the following Formula IV:

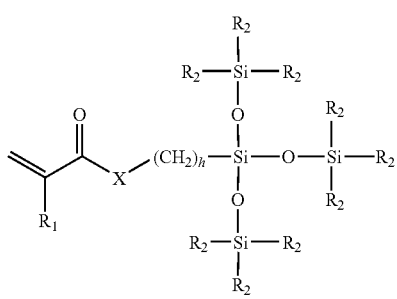

(IV)

wherein:

X denotes —O— or —NR—;

each $R_1$ independently denotes hydrogen or methyl;

each $R_2$ independently denotes a lower alkyl radical, phenyl radical or a group represented by

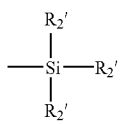

wherein each $R'_{2'}$ independently denotes a lower alkyl or phenyl radical; and h is 1 to 10. Some preferred bulky monomers are methacryloxypropyl tris(trimethyl-siloxy)silane or tris(trimethylsiloxy)silylpropyl methacrylate, sometimes referred to as TRIS.

Another class of representative silicon-containing monomers includes silicon containing vinyl carbonate or vinyl carbamate monomers such as: 1,3-bis[4-vinyloxycarbonyloxy)butyl]tetramethyl-disiloxane; 3-(trimethylsilyl)propyl vinyl carbonate; 3-(vinyloxycarbonylthio)propyl-[tris(trimethylsiloxy)silane]; 3-[tris(trimethylsiloxy)silyl]propyl vinyl carbamate; 3-[tris(trimethylsiloxy)silyl]propyl allyl carbamate; 3-[tris(trimethylsiloxy)silyl]propyl vinyl carbonate; t-butyldimethylsiloxyethyl vinyl carbonate; trimethylsilylethyl vinyl carbonate; and trimethylsilylmethyl vinyl carbonate.

An example of silicon-containing vinyl carbonate or vinyl carbamate monomers are represented by Formula V:

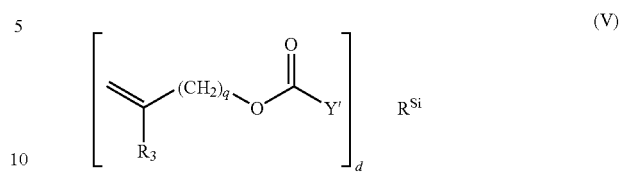

(V)

wherein:

Y' denotes —O—, —S— or —NH—;

$R^{Si}$ denotes a silicon containing organic radical;

$R_3$ denotes hydrogen or methyl;

d is 1, 2, 3 or 4; and q is 0 or 1.

Suitable silicon containing organic radicals $R^{Si}$ include the following:

—$(CH_2)_{n'}Si[(CH_2)_m CH_3]_3$;

—$(CH_2)_{n'}Si[OSi(CH_2)_m CH_3]_3$

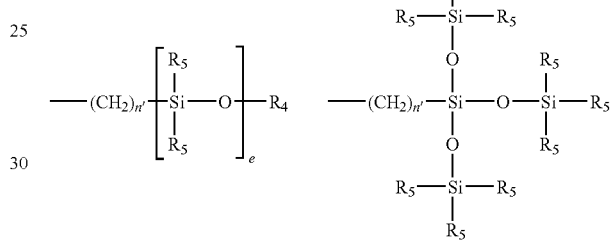

and

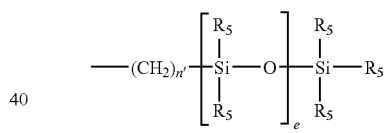

wherein:

$R_4$ denotes

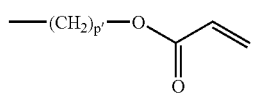

wherein p' is 1 to 6;

$R_5$ denotes an alkyl radical or a fluoroalkyl radical having 1 to 6 carbon atoms;

e is 1 to 200; n' is 1, 2, 3 or 4; and m' is 0, 1, 2, 3, 4 or 5.

An example of a particular species within Formula V is represented by Formula VI.

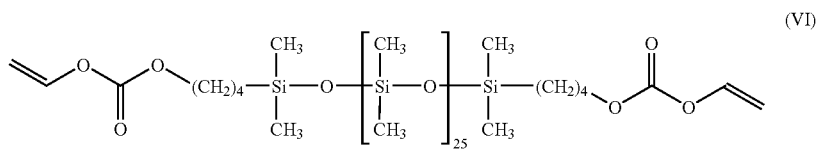

(VI)

Another class of silicon-containing monomers includes polyurethane-polysiloxane macromonomers (also sometimes referred to as prepolymers), which may have hard-soft-hard blocks like traditional urethane elastomers. They may be end-capped with a hydrophilic monomer such as HEMA. Examples of such silicon containing urethanes are disclosed in a variety of publications, including Lai, Yu-Chin, "The Role of Bulky Polysiloxanylalkyl Methacrylates in Polyurethane-Polysiloxane Hydrogels," *Journal of Applied Polymer Science*, Vol. 60, 1193-1199 (1996). PCT Published Application No. WO 96/31792 discloses examples of such monomers, which disclosure is hereby incorporated by reference in its entirety. Further examples of silicon containing urethane monomers are represented by Formulae VII and VIII:

E(*D*A*D*G)$_a$*D*A*D*E'; or  (VII)

E(*D*G*D*A)$_a$*D*G*D*E';  (VIII)

wherein:

D denotes an alkyl diradical, an alkyl cycloalkyl diradical, a cycloalkyl diradical, an aryl diradical or an alkylaryl diradical having 6 to 30 carbon atoms;

G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

a is at least 1;

A denotes a divalent polymeric radical of Formula IX:

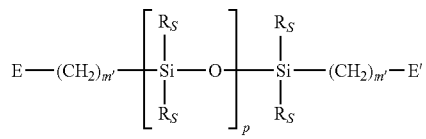

(IX)

wherein:

each $R_s$, independently denotes an alkyl or fluoro-substituted alkyl group having 1 to 10 carbon atoms which may contain ether linkages between carbon atoms;

m' is at least 1; and p is a number which provides a moiety weight of 400 to 10,000;

each of E and E' independently denotes a polymerizable unsaturated organic radical represented by Formula X:

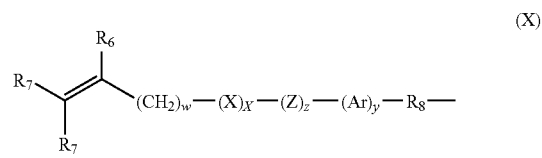

(X)

wherein:

$R_6$ is hydrogen or methyl;

$R_7$ is hydrogen, an alkyl radical having 1 to 6 carbon atoms, or a —CO—Y—$R_9$ radical wherein Y is —O—, —S— or —NH—;

$R_8$ is a divalent alkylene radical having 1 to 10 carbon atoms;

$R_9$ is a alkyl radical having 1 to 12 carbon atoms;

X denotes —CO— or —OCO—;

Z denotes —O— or —NH—;

Ar denotes an aromatic radical having 6 to 30 carbon atoms;

w is 0 to 6; x is 0 or 1; y is 0 or 1; and z is 0 or 1.

A more specific example of a silicon containing urethane monomer is represented by Formula (XI):

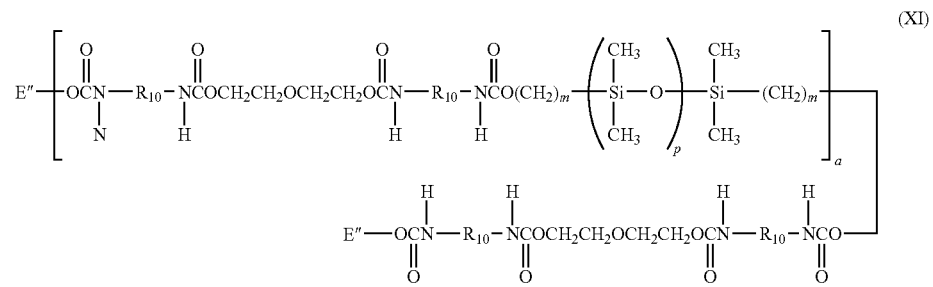

(XI)

wherein m is at least 1 and is preferably 3 or 4, a is at least 1 and preferably is 1, p is a number which provides a moiety weight of 400 to 10,000 and is preferably at least 30, $R_{10}$ is a diradical of a diisocyanate after removal of the isocyanate group, such as the diradical of isophorone diisocyanate, and each E" is a group represented by:

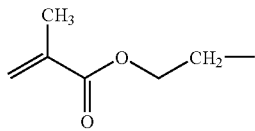

A preferred silicon containing hydrogel material comprises (in the bulk monomer mixture that is copolymerized) 5 to 50 percent, preferably 10 to 25 percent, by weight of one or more silicon containing macromonomers, 5 to 75 percent, preferably 30 to 60 percent, by weight of one or more polysiloxanylalkyl(meth)acrylic monomers, and 10 to 50 percent, preferably 20 to 40 percent, by weight of a hydrophilic monomer. In general, the silicon containing macromonomer is a poly(organosiloxane) capped with an unsaturated group at two or more ends of the molecule. In addition to the end groups in the above structural formulas, U.S. Pat. No. 4,153,641 to Deichert et al. discloses additional unsaturated groups, including acryloxy or methacryloxy. Fumarate-containing materials such as those taught in U.S. Pat. Nos. 5,512,205; 5,449,729; and 5,310,779 to Lai are also useful substrates in accordance with the invention. Preferably, the silane macromonomer is a silicon-containing vinyl carbonate or vinyl carbamate or a polyurethane-polysiloxane having one or more hard-soft-hard blocks and end-capped with a hydrophilic monomer.

Suitable hydrophilic monomers form hydrogels, such as silicon-containing hydrogel materials useful in the present invention. Examples of useful monomers include amides such as dimethylacrylamide, dimethylmethacrylamide, cyclic lactams such as n-vinyl-2-pyrrolidone and poly(alkene glycols) functionalized with polymerizable groups. Examples of useful functionalized poly(alkene glycols) include poly(diethylene glycols) of varying chain length containing monomethacrylate or dimethacrylate end caps. In a preferred embodiment, the poly(alkene glycol) polymer contains at least two alkene glycol monomeric units. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art.

Device Forming Additives and Comonomers

The monomer mix may, further as necessary and within limits not to impair the purpose and effect of the present invention, comprise various additives such as antioxidant, coloring agent, ultraviolet absorber and lubricant.

The monomer mix may be prepared by using, according to the end-use and the like of the resulting shaped polymer articles, one or at least two of the above comonomers and oligomers and, when occasions demand, one or more crosslinking agents.

Where the shaped polymer articles are for example medical products, in particular a contact lens, the monomer mix is suitably prepared from one or more of the silicon compounds, e.g. siloxanyl(meth)acrylate, siloxanyl(meth)acrylamide and silicon containing oligomers, to obtain contact lenses with high oxygen permeability.

The monomer mix may include additional constituents such as crosslinking agents, internal wetting agents, hydrophilic monomeric units, toughening agents, and other constituents as is well known in the art.

Although not required, the monomer mix may include toughening agents, preferably in quantities of less than about 80 weight percent e.g. from about 5 to about 80 weight percent, and more typically from about 20 to about 60 weight percent. Examples of suitable toughening agents are described in U.S. Pat. No. 4,327,203. These agents include cycloalkyl acrylates or methacrylates, such as: methyl acrylate and methacrylate, t-butylcyclohexyl methacrylate, isopropylcyclopentyl acrylate, t-pentylcycloheptyl methacrylate, t-butylcyclohexyl acrylate, isohexylcyclopentyl acrylate and methylisopentyl cyclooctyl acrylate. Additional examples of suitable toughening agents are described in U.S. Pat. No. 4,355,147. This reference describes polycyclic acrylates or methacrylates such as: isobornyl acrylate and methacrylate, dicyclopentadienyl acrylate and methacrylate, adamantyl acrylate and methacrylate, and isopinocamphyl acrylate and methacrylate. Further examples of toughening agents are provided in U.S. Pat. No. 5,270,418. This reference describes branched alkyl hydroxyl cycloalkyl acrylates, methacrylates, acrylamides and methacrylamides. Representative examples include: 4-t-butyl-2-hydroxycyclohexyl methacrylate (TBE); 4-t-butyl-2-hydroxycyclopentyl methacrylate; methacryloxyamino-4-t-butyl-2-hydroxycyclohexane; 6-isopentyl-3-hydroxycyclohexyl methacrylate; and methacryloxyamino-2-isohexyl-5-hydroxycyclopentane.

In particular regard to contact lenses, the fluorination of certain monomers used in the formation of silicon containing hydrogels has been indicated to reduce the accumulation of deposits on contact lenses made therefrom, as described in U.S. Pat. Nos. 4,954,587, 5,079,319, 5,010,141 and 6,891,010. Moreover, the use of silicon containing monomers having certain fluorinated side groups, i.e. —(CF$_2$)—H, have been found to improve compatibility between the hydrophilic and silicon containing monomeric units, as described in U.S. Pat. Nos. 5,387,662 and 5,321,108.

As stated above, surface structure and composition determine many of the physical properties and ultimate uses of solid materials. Characteristics such as wetting, friction, and adhesion or lubricity are largely influenced by surface characteristics. The alteration of surface characteristics is of special significance in biotechnical applications where biocompatibility is of particular concern. Thus, it is desired to provide a silicon containing hydrogel contact lens with an optically clear, hydrophilic surface film that will not only exhibit improved wettability, but which will generally allow the use of a silicon containing hydrogel contact lens in the human eye for extended period of time. In the case of a silicon containing hydrogel lens for extended wear, it be further desirable to provide an improved silicon-containing hydrogel contact lens with an optically clear surface film that will not only exhibit improved lipid and microbial behavior, but which will generally allow the use of a silicon-containing hydrogel contact lens in the human eye for an extended period of time. Such a surface treated lens would be comfortable to wear in actual use and allow for the extended wear of the lens without irritation or other adverse effects to the cornea.

It also be desirable to apply these surface enhancing coatings to implantable medical devices such as intraocular lens materials to reduce the attachment of lens epithelial cells to the implanted device and to reduce friction as the intraocular lens passes through an inserter into the eye.

The present invention is useful for surface treatment of a polymeric device. The surface treatment comprises the binding of interactive segmented block copolymers to the surface of a polymeric medical device substrate by reacting complementary interactive functionalities of the interactive segmented block copolymers with interactive functionalities along the polymeric substrate surface.

As set forth above, for surface modification of contact lenses in accordance with the segmented block copolymers of the present invention, complementary functionality is incorporated between the surface of the contact lens material (i.e., the substrate) and the chemical binding unit block of the interactive segmented block copolymer used as a surface modification treatment polymer (surface modifying agent). For example, if a surface modifying agent has a boronic acid containing functionality, then the contact lens material to be treated must have a residue with complementary functionality that will react with that of the surface modifying agent. In such a case, the contact lens material could include a hydroxyl containing monomer such as 2-Hydroxyethyl methacrylate or glycerol methacrylate to interact with the surface modifying agent boronic acid functionality. Likewise, if a contact lens is formed from material having a residue providing boronic acid, a surface modifying agent containing a 2-hydroxyethyl methacrylate or glycerol methacrylate functionality could be used for surface modification in accordance with the present invention. Such complementary chemical functionality enables binding to occur between the surface of the contact lens and the interactive groups of the one or more surface modifying agent's. This binding between functional groups forms chemical interactions there between. For example, a contact lens containing prepolymer having surface carboxylic acid groups preferably undergo surface modification using surface modifying agents containing quaternary ammonia or other cationic functional groups. Likewise, a contact lens having surface cationic groups preferably undergo surface modification using surface modifying agents containing carboxylic acid units, sulfonic acid units, or other anionic functional units. The reaction of the contact lens containing surface interactive functional groups and the interactive surface modifying agent is conducted under conditions known to those of skill in the art.

In the case where interactive groups are not present in the substrate material, they can be added. For example, by using a surface activation treatment such as oxygen plasma, ammonia-butadiene-ammonia (ABA) treatments and hydrogen-ammonia-butadiene-ammonia (HABA) treatments. Plasma treatment of substrate materials is known and is described in U.S. Pat. No. 6,193,369 Valint et al., U.S. Pat. No. 6,213,604 Valint et al. and U.S. Pat. No. 6,550,915 Grobe, III.

Methods of coating the substrate would include dip coating of the substrate into a solution containing the surface modifying agent. The solution containing the surface modifying agent may contain substantially the surface modifying agent in solvent or may contain other materials such as cleaning and extracting materials. Other methods could include spray coating the device with the surface modifying agent. In order for the covalent bonding reaction to occur, it may be necessary to use suitable catalysts, for example, condensation catalyst. Alternatively, the substrate and the other surface modifying agent may be subjected to autoclave conditions. In certain embodiments, the substrate and the surface modifying agent may be autoclaved in the packaging material that will contain the coated substrate. Once the reaction between the substrate and the surface modifying agent has occurred, the remaining surface modifying agent could be substantially removed and packaging solution would be added to the substrate packaging material. Sealing and other processing steps would then proceed as they usually do. Alternatively, the surface modifying agent could be retained in the substrate packaging material during storage and shipping of the substrate device to the end user.

A general method of coating is now described. Medical devices, such as commercial SofLens59™ contact lenses, are removed from the packaging and soaked in purified water for at least 15 minutes prior to being placed in polymer solution. It should be recognized by persons skilled in the art that the quantities of a solution disclosed herein may be adjusted under specific circumstances to accommodate the size of the medical device. Glass vials are labeled and filled with about 4 ml of a polymer solution, and a lens is placed in each vial. When two polymer solutions are used for coating, they are mixed together immediately prior to placing in the vials. The vials are capped with silicone stoppers and crimped aluminum caps, then placed in an autoclave for one 30-minute cycle. The treated lenses are allowed to cool for a minimum of 3 hours, then removed from the vials and rinsed at least three times with deionized water. The rinsed lenses are then placed into new vials containing 4 ml of borate buffered saline (phosphate for samples undergoing bacterial adhesion testing) and autoclaved for one 30-minute cycle for sterilization.

Other types of contact lenses, such as those comprising other hydrogel materials can be treated with coating polymers, as disclosed above. In one embodiment, PureVision™ contact lenses comprising Balafilcon A hydrogel material, disclosed in U.S. Pat. No. 5,260,000, which is incorporated herein by reference, a surface-treated with a coating polymer as disclosed above. (PureVision™ contact lenses are available from Bausch and Lomb Incorporated, Rochester, N.Y.) In one aspect, PureVision™ contact lenses were first treated with a plasma discharge generated in a chamber containing air and ammonia to increase the population of reactive surface functional groups. A solution for surface treatment comprised segmented block poly(DMA-co-GMA) and poly(acrylic acid).

The silicone hydrogel contact lenses are packaged in a container that includes a receptacle portion to hold the contact lens and a sterile packaging solution. Examples of the container are conventional contact lens blister packages. This receptacle, containing the contact lens immersed in the solution, is hermetically sealed, for example, by sealing lidstock on the package over the receptacle. For example, the lidstock is sealed around a perimeter of the receptacle.

The solution and the contact lens are sterilized while sealed in the package receptacle. Examples of sterilization techniques include subjecting the solution and the contact lens to thermal energy, microwave radiation, gamma radiation or ultraviolet radiation. A specific example involves heating the solution and the contact lens, while sealed in the package container, to a temperature of at least 100° C., more preferably at least 120° C., such as by autoclaving.

The packaging solution is an aqueous solution that includes the interactive segmented block copolymer, preferably in an amount of 0.02 to 5.0 weight percent, based on total weight of the packaging solution. The specific amount of interactive segmented block copolymer will vary depending on the substrate and the copolymer, but generally, the interactive segmented block copolymer will be present in an amount within this range.

The packaging solutions preferably have a pH of about 6.0 to 8.0, more preferably about 6.5 to 7.8, and most preferably 6.7 to 7.7. Suitable buffers include monoethanolamine, diethanolamine, triethanolamine, tromethamine (tris(hydroxymethyl)aminomethane, Tris), Bis-Tris, Bis-Tris Propane, borate, citrate, phosphate, bicarbonate, amino acids, and mixtures thereof. Examples of specific buffering agents include boric acid, sodium borate, potassium citrate, citric acid, Bis-Tris, Bis-Tris Propane, and sodium bicarbonate. When present, buffers will generally be used in amounts ranging from about 0.05 to 2.5 percent by weight, and preferably from 0.1 to 1.5 percent by weight. Some of the interactive surface active segmented block copolymers will act as buffers, and if desired, a supplemental buffering agent may be employed. It has been found that stabilization is dependent on pH, as illustrated in the accompanying examples.

The packaging solutions may further include a tonicity adjusting agent, optionally in the form of a buffering agent, for providing an isotonic or near-isotonic solution having an osmolality of about 200 to 400 mOsm/kg, more preferably about 250 to 350 mOsm/kg. Examples of suitable tonicity adjusting agents include sodium and potassium chloride, dextrose, glycerin, calcium and magnesium chloride. When present, these agents will generally be used in amounts ranging from about 0.01 to 2.5 weight percent and preferably from about 0.2 to about 1.5 weight percent.

Optionally, the packaging solutions may include an antimicrobial agent, but it is preferred that the solutions lack such an agent.

The interactive segmented block copolymers useful in certain embodiments of the present invention may be prepared according to syntheses well known in the art and according to the methods disclosed in the following examples. Surface modification of contact lenses using one or more surface modifying agents in accordance with the present invention is described in still greater detail in the examples that follow.

EXAMPLES

Example A

Synthesis of MAAPBA/DMAPMA-b-NVP Copolymer

To a 500-mL 3-neck round bottom flask equipped with a magnetic stir bar, thermocouple, condenser and SS sparging needle was added 155 mg of AIBN and 1.93-g (0.0094 mol) of 3-methacrylamidophenylboronic acid (MAAPBA). To this was added a solution of 3.21-g (0.0188 mol) N-[3-(dimethylamino)propyl]methacrylamide (DMAPMA) and 0.50-g (0.00236 mol) of benzyl O-ethylxanthate (BX) in 50-mL of methanol. The solution was sparged with argon for 30-min. before applying heat. Separately, in a 250-mL addition funnel, a solution of 49.21-g (0.443 mol) of N-vinylpyrrolidone (NVP) in 200-mL of methanol was sparged with nitrogen for 15 minutes. The addition funnel was transferred to the reaction flask replacing the argon sparging needle. The system was maintained under argon backpressure. The flask was heated to 60° C. and held at that temperature for 6 hours. The NVP solution was subsequently added dropwise to the flask and the polymerization was maintained at 60° C. for an additional 66 hours. The solution was cooled to RT and precipitated dropwise into 6-L of stirred ethyl ether. The precipitate was isolated by filtration and dried in vacuo at 65° C. affording 38.89-g (71%) of white solid. Reprecipitation from 200-mL of methanol into 6-L of ethyl ether gave 37.00-g of product.

The product was characterized by proton NMR (DMSO-d6) and GPC. Resonances attributable to the phenyl protons of MAAPBA were observed at approximately 7.2 to 8.0 ppm. The DMAPMA resonances could not be cleanly distinguished from the PVP resonances. GPC was performed using a PLgel RESIpore column and DMF+1.0 M LiBr as solvent with triple detection. Mn was estimated to be 31,000 Daltons (target=23,300 Daltons) with a polydispersity of 1.09.

Example B

Synthesis of MAAPBA/DMAPMA-b-DMA/MPC Copolymer

To a 500-mL 3-neck round bottom flask equipped with a magnetic stir bar, thermocouple, condenser and SS sparging needle was added 148 mg of AIBN and 1.84-g (0.0090 mol) of 3-methacrylamidophenylboronic acid (MAAPBA). To this was added a solution of 3.06-g (0.0180 mol) N-[3-(dimethylamino)propyl]methacrylamide (DMAPMA) and 0.50-g (0.00225 mol) of ethyl-α-(O-ethylxanthyl) propionate (EEXP) in 50-mL of methanol. The solution was sparged with argon for 25-min. before applying heat. Separately, in a 250-mL addition funnel, a solution of 37.72-g (0.380 mol) of N,N-dimethylacrylamide (DMA) and 12.48-g (0.0423 mol) of 2-methacryloyloxyethyl phosphorylcholine (MPC) in 150-mL of methanol was sparged with nitrogen for 15 minutes. The addition funnel was transferred to the reaction flask replacing the argon sparging needle. The system was maintained under argon backpressure. The flask was heated to 60° C. and held at that temperature for 7 hours. The NVP solution was subsequently added dropwise to the flask and the polymerization was maintained at 60° C. for an additional 48 hours. The solution was cooled to RT and precipitated dropwise into 6-L of stirred ethyl ether. The precipitate was isolated by filtration and dried in vacuo at 65° C. affording 49.05-g (88%) of white solid.

The product was characterized by proton NMR (DMSO-d6) and GPC. Resonances attributable to the phenyl protons of MAAPBA were observed at approximately 7.2 to 8.0 ppm. The DMAPMA resonances could not be cleanly distinguished from the DMA resonances. Resonances attributable to MPC units were observed at 3.2 ppm (trimethylammonium protons) and 3.6 to 4.1 ppm (methylene protons adjacent to oxygen atoms). GPC was performed using a PLgel RESIpore column and DMF+1.0 M LiBr as solvent with triple detection. The polymer did not elute from the column.

Example C

Coating of Contact Lenses with Boronic Acid-Containing Polymers

Contact lenses made of Balafilcon A were cast and processed under standard manufacturing procedures. Balafilcon A is a copolymer comprised of 3-[tris(trimethylsiloxy)silyl] propyl vinyl carbamate, N-vinyl-2-pyrrolidone (NVP), 1,3-bis[4-vinyloxycarbonyloxy)but-1-yl]polydimethylsiloxane and N-vinyloxycarbonyl alanine. All Balafilcon A lenses were air-plasma treated prior to exposure to coating polymer ("Test" Groups) or just standard borate-buffered saline solution containing 300 ppm EDTA ("Control" Groups), below.

For coating with the subject polymers, each lens was placed in a polypropylene (PP) blister containing 3.8-mL of a 100 or 250 ppm (w/v) solution of the subject polymer dissolved in borate-buffered saline (BBS) containing 300 ppm EDTA. The blisters were sealed and autoclaved at 121° C. for 30-min.

Table 2 reports various surface properties of several coated samples and controls. Test sample A was coated with the polymer of Example A, and Test sample B was coated with the polymer of Example B. Atomic concentrations were determined by XPS, as described below.

TABLE 2

| | XPS Atomic Concentrations | | | |
|---|---|---|---|---|
| | % C | % O | % N | % Si |
| Test Sample A (100 ppm) | 67.5 +/− 0.7 | 18.4 +/− 0.2 | 8.9 +/− 0.5 | 5.2 +/− 0.2 |
| Test Sample A (250 ppm) | 68.1 +/− 0.5 | 18.1 +/− 0.5 | 9.0 +/− 0.4 | 4.8 +/− 0.3 |
| Control Sample A | 63.7 +/− 0.6 | 20.7 +/− 0.2 | 7.6 +/− 0.4 | 7.4 +/− 0.4 |
| Test Sample B (100 ppm) | 66.9 +/− 1.0 | 19.3 +/− 0.5 | 9.2 +/− 0.4 | 4.7 +/− 0.4 |
| Test Sample B (250 ppm) | 66.9 +/− 0.5 | 19.1 +/− 0.6 | 9.4 +/− 0.4 | 4.5 +/− 0.3 |
| Control Sample B | 63.0 +/− 0.5 | 21.5 +/− 0.4 | 7.5 +/− 0.2 | 7.1 +/− 0.2 |

X-ray Photoelectron Spectroscopy (XPS) Analysis

XPS data was collected using a Physical Electronics Quantera SXM Scanning ESCA Microprobe. This instrument utilizes a monochromatic Al anode operated at 18 kV and 100 Watts in the high power mode and 15 kV and 0.25 Watts/micron in low power mode. All high power acquisitions are rastered over a 1400 micron×100 micron analysis area. Dual beam neutralization (ions and electrons) is used. The base pressure of the instrument was $5 \times 10^{-10}$ torr and during operation the pressure was less than or equal to $1 \times 10^{-7}$ torr. This instrument made use of a hemispherical analyzer operated in FAT mode. A gauze lens was coupled to a hemispherical analyzer in order to increase signal throughput. Assuming the inelastic mean free path for a carbon 1 s photoelectron is 35 Å, the practical measure for sampling depth for this instrument at a sampling angle of 45 is approximately 75 Å. The governing equation for sampling depth in XPS is:

$$\theta \lambda \sin 3 = d$$

where d is the sampling depth, λ is the photoelectron inelastic mean free path and θ is the angle formed between the sample surface and the axis of the analyzer. Each specimen was analyzed utilizing a low-resolution survey spectra (0-1100 eV) to identify the elements present on the sample surface. Quantification of elemental compositions was completed by integration of the photoelectron peak areas. Analyzer transmission, photoelectron cross-sections and source angle correction were taken into consideration in order to give accurate atomic concentration values.

Example D

Synthesis of DMA-b-DMAPMA/MAAPBA/DMA

To a 500-mL 3-neck round bottom flask containing a magnetic stir bar, addition funnel and thermocouple was added 0.033-g AIBN (20 mol % based on amount of RAFT agent), 0.354-g (0.0010 mol) 2-(dodecylthiocarbonylthio)propanoic acid, 20.0-g (0.202-mol) of distilled N,N-dimethylacrylamide (DMA) and 80-mL of dioxane. The addition funnel was charged with a solution of 1.37-g (0.0081-mol) of deinhibited and distilled N-[3-(dimethylamino)propyl]methacrylamide (DMAPMA), 0.83-g (0.0040-mol) of 3-methacrylamidophenylboronic acid (MAAPBA) and 1.20-g (0.121-mol) of distilled N,N-dimethylacrylamide (DMA) in 30 mL dioxane. Both solutions were individually sparged with nitrogen for at least 30-min before heating and were subsequently maintained under a nitrogen blanket for the duration of the reaction. The reaction was heated to 60° C. After 2.75 h, the addition funnel contents were added to the reaction flask. Heating was discontinued after 12 h total heating time at which point the cooled solution was added drop wise to 6 L of mechanically stirred ethyl ether. The precipitate was isolated by vacuum filtration. The solid was dried in vacuo at 40° C. for a minimum of 18 hours, affording 22.55-g of pale yellow solid.

To remove the RAFT end group, the copolymer was dissolved in 100-mL 2-propanol containing 0.53-g (0.0032-mol) of AIBN. The solution was sparged with nitrogen for 1 h and then heated at 80° C. for 12 h under a nitrogen blanket. The cooled solution was precipitated by dropwise addition into 6-L of mechanically stirred ethyl ether. The white solid was collected by vacuum filtration and vacuum dried at 85° C. giving 18.75-g of product.

*Note: This polymerization yields a block copolymer, PDMA-block-(DMAPMA/MAAPBA/DMA), in which the second block is actually a statistical copolymerization of any remaining DMA that had not been polymerized at the time of the DMAPMA, MAAPBA, and DMA addition. The second "block", is therefore compositionally heterogeneous. A polymerization that yields a statistical copolymerization or compositionally heterogeneous block as the second block would also be considered to be a reactive segmented block copolymer according to the invention herein.

The product was characterized by proton NMR (methanol-d4), GPC, Karl-Fischer and elemental analysis. Resonances attributable to the phenyl protons of MAAPBA were observed at approximately 7.1 to 7.8 ppm. The DMAPMA resonances could not be cleanly distinguished from DMA resonances. GPC was performed at 35° C. in DMF containing 0.01 M lithium nitrate. The column set consisted of three 8-mm by 300-mm GRAM Linear M columns from Polymer Standards Services. Narrow MW PMMA reference standards were used for calibration. The primary peak had a Mn of 17,900 (target=23,200) with a polydispersity of 1.8. The results for elemental analysis were:

TABLE 3

| Element | Calculated | Found |
|---|---|---|
| C | 60.6% | 59.5% |
| H | 9.1% | 9.2% |
| N | 14.0% | 13.7% |
| O | 16.1% | 17.7% |
| B | 0.19% | 0.16% |
| S | trace | 300 ppm |

*Water content by Karl-Fischer analysis was 1.7%

Example F

Coating of Contact Lenses with Poly DMA-b-DMAPMA/MAAPBA/DMA

Contact lenses made of Balafilcon A were cast and processed under standard manufacturing procedures. All Balafilcon lenses were air-plasma treated prior to exposure to coating polymer ("Test" Groups) or standard borate-buffered saline (BBS) containing 300 ppm EDTA.

For coating with the subject polymers, each lens was placed in a polypropylene (PP) blister containing 3.8-mL of a 500 ppm (w/v) solution of subject polymer dissolved in BBS containing 300 ppm EDTA. The lens blisters were sealed and autoclaved at 121° C. for 30-min.

TABLE 4

|  | % C | % O | % N | % Si |
|---|---|---|---|---|
| Test Sample (500 ppm polymer) | 67.5 (0.4) | 18.6 (0.1) | 10.2 (0.7) | 3.8 (0.3) |
| Control Sample (BBS) | 63.2 (0.7) | 21.9 (0.5) | 7.6 (0.3) | 7.1 (0.3) |

Example G

Synthesis of a Matrix of GMA-b-DMA Copolymers where the MW of Each of the Blocks is Varied (Demonstrates Control of MW with CRP)

TABLE 5

| Reaction | DMA (mL) | DMA (mol) | CTR (mgs) | CTR (mol) | GMA (mL) | GMA (mol) | MW DMA block (theoretical) | MW GMA block (theoretical) |
|---|---|---|---|---|---|---|---|---|
| 2748-114 | 20 | 0.194 | 350 | 0.00097 | 2.0 | 0.0146 | 19,800 | 2,140 |
| 2748-115 | 20 | 0.194 | 350 | 0.00097 | 4.0 | 0.0293 | 19,800 | 4,275 |
| 2748-116 | 20 | 0.194 | 350 | 0.00097 | 8.0 | 0.0586 | 19,800 | 8,550 |
| 2748-117 | 20 | 0.194 | 700 | 0.00194 | 2.0 | 0.0146 | 9,900 | 1,070 |
| 2748-118 | 20 | 0.194 | 700 | 0.00194 | 4.0 | 0.0293 | 9,900 | 2,140 |
| 2748-119 | 20 | 0.194 | 700 | 0.00194 | 8.0 | 0.0586 | 9,900 | 4,275 |
| 2748-120 | 10 | 0.097 | 700 | 0.00194 | 2.0 | 0.0146 | 4,950 | 1,070 |
| 2748-121 | 10 | 0.097 | 700 | 0.00194 | 4.0 | 0.0293 | 4,950 | 2,140 |
| 2748-122 | 10 | 0.097 | 700 | 0.00194 | 8.0 | 0.0586 | 4,950 | 4,275 |

*~33 mgs of AIBN were added to all of the reactions

*Note: All reactions were carried out in a similar fashion using the amounts shown in the table above. Reaction 2748-114 is described below as an example of the procedure used. Weighed 350 mgs (0.97 mmol) of S-1-Dodecyl-S-(α,α'-dimethyl-α"-acetic acid) trithiocarbonate and 33 mgs of AIBN into a 250 ml round bottom flask. Added 20 ml (194 mmol) of N,N-Dimethylacrylamide (DMA) and 60 ml of dioxane to the flask, sealed flask with a septum and then purged with argon to deoxygenate for 30 mins. Placed flask in an oil bath (50° C.) for 6.0 hrs. In a separate container, 2.0 ml (14.66 mmol) of glycidyl methacrylate (GMA) was bubbled with argon for 30 mins., then added to the flask after 6.0 hrs. *Note: A small aliquot was taken from the flask immediately before GMA addition and precipitated into diethyl ether. The reaction was stopped 15 hours after GMA addition (19.5 hrs total reaction time). The final product was precipitated out of the reaction mixture into diethyl ether.

Both the first precipitate and the block copolymer of DMA and GMA were characterized by proton NMR (CDCl3) and GPC. The GPC shows a shift in the elution peak to shorter times (higher MW) after the addition of the GMA block. In addition, the NMR spectra of the block copolymer shows peaks for the glycidol methacrylate contributions at 3.7 ppm and 4.3 ppm. GPC data for these polymers using DMF as an eluent are shown below, using both PMMA standards and PVP standards as calibrants. Although the trends in MW are the same, PMMA standards show MW's much closer to the theoretically expected value for polyDMA.

TABLE 6

| Sample | PMMA Standards | | PVP Standards | |
|---|---|---|---|---|
|  | Mw | Mn | Mw | Mn |
| 2748-114 | 20,270 | 15,320 | 432,500 | 207,100 |
| 2748-115 | — | — | 534,200 | 219,500 |
| 2748-116 | — | — | 681,500 | 282,000 |
| 2748-117 | 8,950 | 6,430 | 147,800 | 71,700 |
| 2748-118 | — | — | 182,400 | 74,100 |
| 2748-119 | — | — | 245,900 | 72,300 |
| 2748-120 | 4,000 | 2,540 | 48,600 | 16,100 |

TABLE 6-continued

| Sample | PMMA Standards | | PVP Standards | |
|---|---|---|---|---|
|  | Mw | Mn | Mw | Mn |
| 2748-121 | — | — | 70,100 | 15,000 |
| 2748-122 | — | — | 145,100 | 20,0 |

Example H

Synthesis of DMA-b-TMAQPMA

Weighed 350 mgs (0.97 mmol) of S-1-Dodecyl-S-(α, α'-dimethyl-α"-acetic acid) trithiocarbonate and 35 mgs of AIBN into a 250 ml round bottom flask. Added 10 ml (97 mmol) of N,N-Dimethylacrylamide (DMA) and 30 ml of dioxane to the flask, sealed flask with a septum and then purged with argon to deoxygenate for 30 mins. Placed flask in an oil bath (50° C.) for 6.0 hrs. In a separate container, 2.52 grams (14.8 mmol) of N,N-dimethylaminopropyl methacrylate (DMAPMA) was bubbled with argon for 30 mins., then added to the flask after 6.0 hrs. *Note: A small aliquot was taken from the flask immediately before DMAPMA addition and precipitated into diethyl ether. The reaction was stopped 16 hours after addition (22 hrs total reaction time). The final product was precipitated out of the reaction mixture into diethyl ether.

Both the first precipitate and the block copolymer of DMA and DMAPMA were characterized by proton NMR (CDCl3)

and GPC. The GPC shows a shift in the elution peak to shorter times (higher MW) after the addition of the DMAPMA block. (Mn shifts from 11,000 Daltons to 12,000 Daltons using PMMA standards). In addition, in the NMR spectra the DMAPMA resonances could not be cleanly distinguished from the DMA resonances, however the influence of the N-methyl resonances could be seen at around 2.2 ppm (shape of the peak changed).

In a second quaternization step, 2 grams of the dried polymer precipitated above was dissolved in 15 mL of N,N-dimethylformamide. To this reaction was added 1.0 mL of Iodomethane (stoichiometric excess). The reaction was stirred overnight, concentrated on the rotary evaporator, and then dissolved in methanol and precipitated into diethyl ether. This reaction yielded the block copolymer DMA-b-TMAQPMA*TMAPQMA=Trimethylaminoquat propyl methacrylate.

Example I

Synthesis of DMA-b-MAA

Weighed 350 mgs (0.97 mmol) of S-1-Dodecyl-S-($\alpha$, $\alpha'$-dimethyl-$\alpha''$-acetic acid) trithiocarbonate and 35 mgs of AIBN into a 250 ml round bottom flask. Added 10 ml (97 mmol) of N,N-Dimethylacrylamide (DMA) and 30 ml of dioxane to the flask, sealed flask with a septum and then purged with argon to deoxygenate for 30 mins. Placed flask in an oil bath (50° C.) for 6.0 hrs. In a separate container, 2.31 grams (14.6 mmol) of trimethylsilyl methacrylate (TMS-MA) was bubbled with argon for 30 mins., then added to the flask after 6.0 hrs. *Note: A small aliquot was taken from the flask immediately before TMS-MA addition and precipitated into diethyl ether. The reaction was stopped 16 hours after addition (22 hrs total reaction time). The final product was precipitated out of the reaction mixture into diethyl ether.

Both the first precipitate and the block copolymer of DMA and TMS-MA were characterized by proton NMR (CDCl3) and GPC. The GPC shows a shift in the elution peak to shorter times (higher MW) after the addition of the TMS-MA block. In addition, the NMR spectra contained proton resonances at 0 ppm from the trimethylsilyl units.

In a second deprotection step, 3 grams of the dried polymer precipitated above was dissolved in 20 mL of dioxane, 1.0 mL of water, and 1.0 mL of glacial acetic acid. The reaction was stirred for 2 hours at 50° C., concentrated on the rotary evaporator, and precipitated into diethyl ether. This reaction yielded the block copolymer DMA-b-MAA.

While there is shown and described herein certain specific structures and compositions of the present invention, it will be manifest to those skilled in the art that various modifications may be made without departing from the spirit and scope of the underlying inventive concept and that the same is not limited to particular structures herein shown and described except insofar as indicated by the scope of the appended claims.

What is claimed is:

1. A method of forming a surface modified medical device, the method comprising:
    providing a medical device having at least one group providing interactive functionality on at least one surface of the medical device, wherein the medical device comprises hydrogel materials;
    providing a surface modifying agent comprising an interactive segmented block copolymer having a structure selected from the following structural formulas I-III:

$$R1-[(A)m]p-[(B)n]q-X \qquad (I),$$

$$R1-[(A)m]p-[(B)n]q-R2, \text{ and} \qquad (II)$$

$$R1-[(B)n]q-[(A)m]p-R2-[(A)m]p-[(B)n]q-R1 \qquad (III)$$

wherein R1 is a reactive residue of a moiety capable of acting as an initiator for Atom Transfer Radical Polymerization, a radical forming residue of a Reversible addition-fragmentation chain transfer polymerization agent or a free radical initiator; R2 is a thio carbonyl thio group, thio carbonyl fragment of a chain transfer agent or a derivatized reaction product; A is a chemical binding unit block, B is a hydrophilic unit block, m is 1 to 10,000, n is 1 to 10,000, p and q are natural numbers, and X is a halogen capping group of an initiator for Atom Transfer Radical Polymerization or a derivatized reaction product
    contacting the at least one surface having interactive functionality of the medical device with the surface modifying agent, and;
    subjecting the device surface and surface modifying agent to reaction conditions suitable for forming a chemical interaction selected from the group consisting of electrostatic or complexation interaction between the device surface and the surface modifying agent to form a surface modified medical device.

2. The method of claim 1 wherein the medical device is prepared from a silicon containing monomer.

3. The method of claim 2 wherein the silicon containing monomer comprises a silicon containing monomer selected from the group consisting of silicon containing vinyl carbonates, silicon containing vinyl carbamates, polyurethane-polysiloxanes having one or more hard-soft-hard blocks and end-capped with a hydrophilic monomer, fumarate containing silicon containing monomers, poly(organosiloxanes) capped with an unsaturated group at two or more ends of the molecule, polyurethane-polysiloxane macromonomers and mixtures thereof.

4. The method of claim 2 wherein the medical device comprises as a bulk monomer mixture to be copolymerized 5 to 50 percent by weight of one or more silicon containing macromonomers, 5 to 75 percent by weight of one or more polysiloxanylalkyl (meth)acrylic monomers, and 10 to 50 percent by weight of a hydrophilic monomer.

5. The method of claim 2 wherein the medical device comprises as a bulk monomer mixture to be copolymerized 10 to 25 percent by weight of one or more silicon containing macromonomers, 30 to 60 percent by weight of one or more polysiloxanylalkyl(meth)acrylic monomers, and 20 to 40 percent by weight of a hydrophilic monomer.

6. The method of claim 1 wherein the medical device comprises vinyl functionalized polydimethylsiloxanes copolymerized with hydrophilic monomers.

7. The method of claim 1 wherein the medical device comprises fluorinated monomers.

8. The method of claim 1 wherein the medical device comprises methacrylate functionalized fluorinated polyethylene oxides copolymerized with hydrophilic monomers.

9. The method of claim 1 wherein the medical device is selected from the group consisting of heart valves, intraocular lenses, intraocular lens inserters, contact lenses, intrauterine devices, vessel substitutes, artificial ureters, vascular stents, phakic intraocular lenses, aphakic intraocular lenses, corneal implants, catheters, implants, and artificial breast tissue.

10. The method of claim 9 wherein the medical device formed is a soft contact lens.

11. The method of claim 10 wherein the medical device is a silicon containing hydrogel contact lens material.

12. The method of claim 1, wherein the interactive segmented block copolymer has the chemical binding unit is a monomer selected from the group consisting of styrene boronic acid, 3-methacrylamido styrene boronic acid, 2-methacryloyloxyethylsulfonate salts, 3-methacrylamidopropyl-N,N,N-trimethyammonium salts, 2-methacryloyloxyethyl-N,N,N-trimethylammonium salts, and amine-containing monomers, such as 3-methacrylamidopropyl-N,N-dimethyl amine.

13. The method of claim 1, wherein the interactive segmented block copolymer has a hydrophilic unit monomer selected from the group consisting of 2-hydroxyethyl methacrylate, glycerol methacrylate, methacrylic acid, acrylic acid, methacrylamide, acrylamide, N,N'-dimethylmethacrylamide, N,N'-dimethylacrylamide; ethylenically unsaturated poly(alkylene oxide)s, cyclic lactams, N-vinyl-2-pyrrolidone, vinyl carbonate, vinyl carbamate, 2-hydroxyethyl acrylate, 2-(2-ethoxyethoxy)ethyl(meth)acrylate, glyceryl(meth)acrylate, poly(ethylene glycol (meth)acrylate), tetrahydrofurfuryl(meth)acrylate, N-vinyl acetamide and copolymers, derivatives and combinations thereof.

14. The method of claim 1, wherein the interactive segmented block copolymer has a chemical binding unit comprises between 1 and about 1,000 units.

15. The method of claim 1, wherein the interactive segmented block copolymer has a chemical binding unit comprises between 1 and about 100 units.

16. The method of claim 1, wherein the interactive segmented block copolymer has a chemical binding unit comprising between 1 and about 30 units.

17. The method of claim 1, wherein the interactive segmented block copolymer has a hydrophilic block comprising between 1 and about 10,000 units.

18. The method of claim 1, wherein the interactive segmented block copolymer has a hydrophilic block comprising between about 10 and about 1,000 units.

19. The method of claim 1, wherein the interactive segmented block copolymer has a hydrophilic block comprising between about 20 and about 300 units.

* * * * *